United States Patent [19]

Pickhard

[11] Patent Number: 4,720,285

[45] Date of Patent: Jan. 19, 1988

[54] INJECTION SYRINGE

[76] Inventor: Ewald Pickhard, Redtenbachergasse 15, A-1160 Vienna, Austria

[21] Appl. No.: 893,297

[22] PCT Filed: Nov. 20, 1985

[86] PCT No.: PCT/AT85/00048

§ 371 Date: Jul. 21, 1986

§ 102(e) Date: Jul. 21, 1986

[87] PCT Pub. No.: WO86/03126

PCT Pub. Date: Jun. 5, 1986

[30] Foreign Application Priority Data

Nov. 21, 1984 [AT] Austria .................. 3688/84

[51] Int. Cl.[4] ............................................. A61M 5/32
[52] U.S. Cl. .................. 604/192; 604/206; 604/240; 604/263
[58] Field of Search ............... 604/187, 192, 201, 240, 604/205, 206, 263, 86, 87, 88

[56] References Cited

U.S. PATENT DOCUMENTS

| | | | |
|---|---|---|---|
| 2,828,742 | 4/1958 | Ashkenaz | 604/206 X |
| 3,073,307 | 1/1963 | Stevens | 604/192 |
| 3,989,044 | 11/1976 | Meierhoefer | 604/201 X |
| 4,249,530 | 2/1981 | Millet | 604/240 X |
| 4,281,653 | 8/1981 | Barta et al. | 605/240 X |
| 4,334,536 | 6/1982 | Pfleger | 604/201 |

FOREIGN PATENT DOCUMENTS 577727 6/1933 Fed. Rep. of Germany ...... 604/205
2434046 1/1976 Fed. Rep. of Germany .

Primary Examiner—John D. Yasko
Attorney, Agent, or Firm—Kurt Kelman

[57] ABSTRACT

The invention specifies an injection syringe comprising a syringe body.

A needle carrier receiving the syringe needle is inserted into the same. A securing device joined to the needle carrier in force-locked and/or shape-locked manner and which may be coupled to a coupling member of the syringe body in at least partially shape-locked manner, is provided furthermore. The syringe needle has allocated to it a needle protection cap which is enveloping and extends into the area of the needle carrier. An opening device is situated between the needle carrier (5,26,50,61) and the extremity of the needle protection cap (12,25) allocated to the needle tip. This may be formed by a weakening line (14,23,46).

3 Claims, 5 Drawing Figures

U.S. Patent  Jan. 19, 1988  Sheet 1 of 3  4,720,285
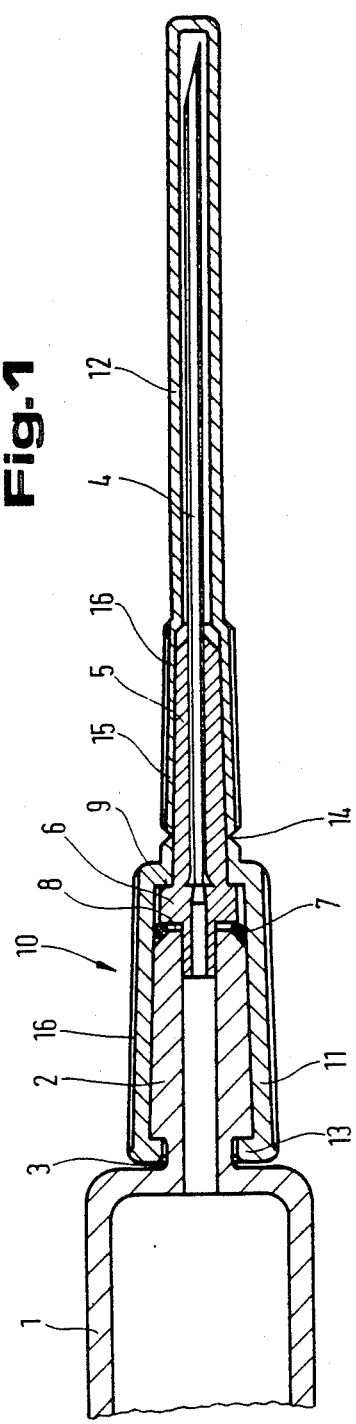
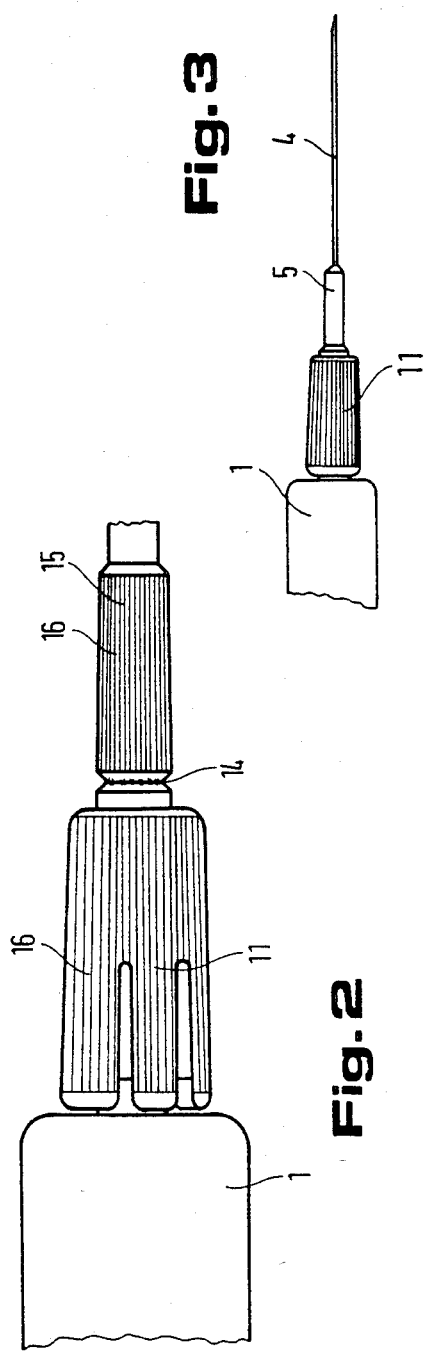

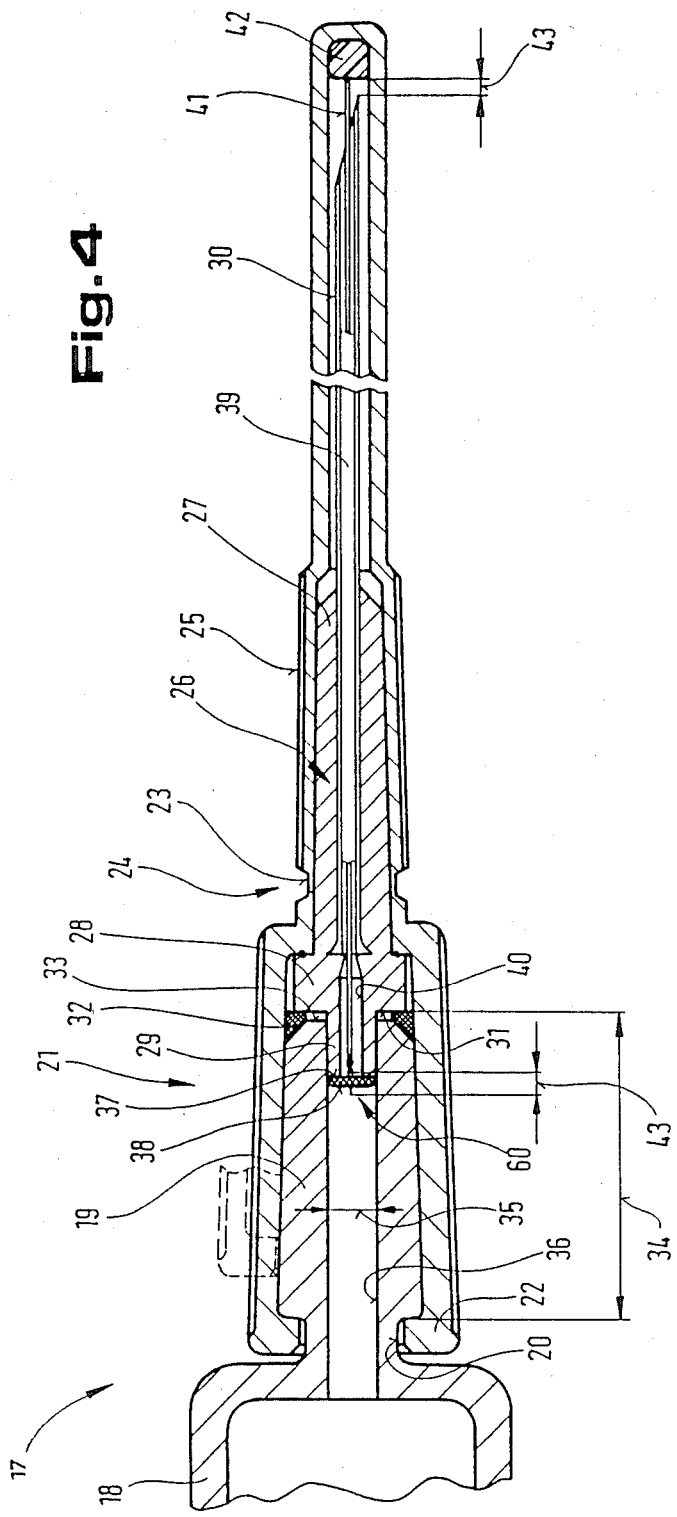

INJECTION SYRINGE

The invention relates to an injection syringe.

In the case of disposable injection syringes, it is known to provide withdrawable caps for protection of the syringe needle, during transport and to reduce the risk of an injury. As a rule, the injection syringe is assembled with a syringe needle of this kind only just before utilisation.

In the case of packaging comestible and luxury food products, and pharmaceuticals which are to be administered, it is known to provide a security closure which makes it possible to discover whether a package has been broached or opened, or not. In the case of injection needles, it is known furthermore to store these in a plastics material container, for example a plastics material bag, packed in sterile manner under welded seal.

The invention has as its object an injection syringe comprising an already attached needle which is packaged in sterile manner from the time of filling and until its utilisation, without any complementary protective measures. Furthermore, the injection syringe should be openable only in a manner which subsequently clearly discloses the fact that the syringe had already been opened.

The object of the invention is accomplished with an injection syringe comprising a syringe body adapted to receive an injection fluid and a frusto-conically tapered attachment member integral with the syringe body, the syringe body and the attachment member defining an annular groove therebetween, and the attachment member defining an outlet opening for the injection fluid in communication with the syringe body. A membrane closes the outlet opening. A syringe needle is arranged coaxially with the outlet opening and a tubular needle element is arranged coaxially with the outlet opening and in communication with the syringe needle, the tubular needle element having an end facing the membrane and the membrane being interposed between the tubular needle element end and the outlet opening. The injection syringe further comprises a two-part protective cap for the syringe needle, one part of the cap constituting a securing device for the cap and including inwardly projecting claw means resiliently engaging the annular groove, a second part of the cap constituting a needle protection cap, and a weakened score line frangibly connects the parts of the protective cap. A two-part device for breaking the membrane whereby the outlet opening communicates with the tubular needle element extends in the interior of the protective cap from the attachment member past the score line to the needle protection cap and essentially consists of a needle carrier part joined to the protective cap and defining an axial bore having an open end facing the membrane, a support member part joined to the tubular needle element, the support member holding the syringe needle and the support member with the tubular needle element being displaceably guided in the needle carrier part relative to the membrane in a direction of the longitudinal extension of the syringe needle for piercing the membrane, and the tubular needle element being sealingly and slidably guided in the needle carrier.

In such an injection syringe, the needle protection cap itself may be utilised for a security seal or closure. Other advantages of the structure according to the invention emerge from the fact that the needle protection cap may assure the force-locked connection of the needle with the attachment member of the phial, simultaneously with its base element, a sterile seal being secured in this area at the same time. If, for example, the needle protection cap is joined to the needle carrier by welding or bonding, it is possible to secure a simple snap-on joint, in which the needle carrier is sealingly kept in contact with the attachment member, the sterility is maintained by means of the sealing surfaces and a contamination is prevented. This snap-on joint is not releasable without a tool, and since it is possible to select conventional materials as the material of the protective cap, for example plastics materials, the application of tools leaves traces detectable with certainty. For utilisation of the syringe, merely the opening device is removed, e.g. the weakening score line which is severed, and this is readily possible without application of tools.

The provision of the closing membrane has the advantage that the medication is kept exclusively in the sryinge body and that a penetration by air is reliably prevented. Furthermore, the sterility of the injection syringe is maintained as before, by incorporation of the score line opening element within the needle protection cap. By the utilisation of two elements displaceable with respect to each other, in combination with a membrane, it is assured that the sterility of the injection syringe is retained even upon opening the diaphragm.

For a clearer grasp of the invention, the same is described in particular in the following with reference to the embodiments illustrated in the drawings wherein, FIG. 1 shows an injection syringe according to the invention, with a needle protection cap attached thereto, in axial cross-section;

FIG. 2 shows a partial view of the injection syringe according to FIG. 1 before utilisation;

FIG. 3 shows a reduced partial view of the injection syringe according to FIG. 2 after removal of the front portion of the needle protection cap;

FIG. 4 shows a modified embodiment of an injection syringe according to the invention, comprising a closure device situated in line with the syringe channel and an associated opening device situated inside the needle protection cap.

Figure 5:
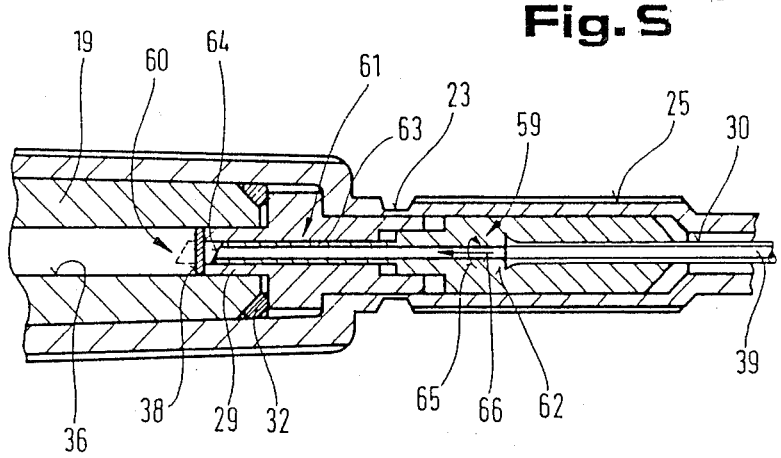
FIG. 5 shows a modified embodiment of a fragmentary view of a closure device for an injection syringe according to the invention in axial cross-section.

In FIG. 1, the syringe body receiving the injection fluid is denoted by 1. The syringe body has a tapered attachment member 2 which is integrally formed with the syringe body 1. An annular groove 3 is arranged at the point of transition between the attachment member 2 and the syringe body 1, as a groove-shaped depression. A syringe needle 4 is connected to a needle carrier 5, preferentially being co-moulded with the same. The neelde carrier 5 has an annular flange 6 which may be thrust against an end face 8 of the attachment member 2 facing towards the needle carrier 5, and a seal 7 is interposed between end face 8 and flange 6. At its end face 9 facing towards the syringe needle 4, the annular flange 6 is joined to a two-part protective cap 10 comprising a securing device 11 and a needle protection cap 12, the joint being obtained by ultrasonic welding.

When assembling the injection syringe for simultaneously securing a sterile closure, the unit comprising the needle carrier 5, syringe needle 4 and protective cap 10 is pushed on to the tapered external surface of the attachment member 2, inwardly projecting claws 13 of the securing device 11 of the protective cap 10 acting as a base element, engaging in the annular groove 3.

Apart from the base element for force-locked connection of the needle carrier 5 to the attachment member 2, the protective cap 10 comprises the needle protection cap 12 surrounding the needle and joined to the base element line 14.

It is apparent from FIG. 1 that the securing device 11 acting as the base element, as well as a portion 15 of the needle protection cap 12 surrounding the needle carrier 5, comprise grooving 16. The handling capacity, in particular the rotatability of the two parts with respect to each other for the purpose of breaking them apart at score line 14, is improved in this manner.

After severing the two parts, the needle protection cap 12 engaging over the needle may be pulled off the protective cap 10 and the injection syringe may be utilised immediately. An injection syringe of this kind is illustrated with the needle cap pulled off, in FIG. 3.

A syringe body 18 consisting of glass in most cases, which has integrally formed with it an attachment member 19, a groove-like depression being situated between the sryinge body 18 and the attachment member 19 as a connecting element, and forming part of an injection syringe 17, is shown in FIG. 4. The attachment member 19 has engaged over it a securing device 21 or rather its tapered jacket, which at the extremity turned towards the syringe body 18 engages with claw-like projections 22 in the groove-like depression 20 between the attachment member 19 and syringe body 18. This projection may be formed by an encircling annular bead or by several claws engaging only segments of the tapered jacket. The securing device 21 is integrally joined to a needle protection cap 25 by an opening device 24 formed by a score line 23. The securing device 21 is moreover joined to a needle carrier 26 in force-locked and shape-comforing manner, for example by an ultrasonic welding operation. This needle carrier 26 comprises a support member 27 which may preferentially be conically formed as in the present embodiment, an annular flange 28 adjacent thereto and a locating or guiding element 29 in the direction of the syringe body 18. This needle carrier 26 is preferentially injection molded with the syringe needle 30. An end face 31 of the annular flange 28 preferably bears via a seal 32, for example an O-ring, against an end face 33 of the attachment member 19 facing towards the needle carrier. A distance 34 between one flank of the groove-like depression 20 and the end face 31 substantially corresponds to a distance between the same lateral flank of the groove-like depression and the end face 33 of the attachment member 19. It is primarily when no seal 32 is provided, that the distance 34 is a little smaller in the unstressed condition of the projection 22 than the corresponding distance of the attachment member, to assure reliable contact of the end face 31 with the end face 33 of the attachment member 19 and thus of an absolute hermetical seal. In the embodiment illustrated, the locating element 29 has approximately the same diameter 35 as an outlet opening 36 of the attachment member 19. A length of the locating element 29 in the direction of the outlet opening 36 is so dimensioned that it is greater than a thickness of the projection 22 provided in the same direction, so that whilst the projections 22 have snapped from the expanded position indicated by pecked lines into the snapped-in position shown by solid lines, a central location of the securing device 21 with the locating element 29 in the outlet opening 36 is assured. A central seat of the needle carrier 26 and a precise seal between the needle carrier 26 and the attachment member 19 are secured thereby.

A closure device formed by a liquid-tight diaphragm 38 may be situated in the area of an end face 37 of guiding elements 29 facing towards the syringe body 18. An opening device formed by a needle 41 is installed for piercing this diaphragm and for establishing a communication between the outlet opening 36 and an injection extremity of the syringe needle 30, or between the syringe needle channel 39 situated in the syringe needle, and an injection channel 40 in the needle carrier 26. The needle 41 of the opening device extends from the extremity of the needle protection cap 25 associated with the tip of the injection needle 30 to just before the diaphragm 38. If the needle protection cap 25 is opened by being twisted with respect to the securing device 21, for which purpose the two elements last referred to may, as apparent from the drawing, be provided—as already shown in FIGS. 1 to 3—with grooving, or with actuating flanges, and the needle protection cap 25 is pulled off, the needle tip may be pushed forward along a distance 43 by means of an actuating element 42 situated on the needle extremity, so that the needle tip pierces the diaphragm 38 and establishes a communication between the syringe needle channel 39 and the outlet opening 36. After it has pierced th diaphragm, the needle 41 is drawn out with the actuating element 42 and the injection syringe 17 is ready for injection of the injection solution. The piston provided for this purpose in the syringe body 18, and the actuating device for the same, as well as the injection solution, are not illustrated and any such known devices may be utilised for this purpose.

Another modified embodiment of an opening element 59 for a closure device 60 formed by a diaphragm 38, is shown in FIG. 5. The original closure or opening device of a needle protection cap 25 is again constructed in accordance with one of the previously described embodiments. The opening element 59 for the diaphragm 38 is however formed in the present embodiment by the fact that a needle carrier 61 is associated with a support member element 62 displaceable with respect to the same, wherein the syringe needle 30 is integrally co-moulded. This support member element 62 comprises a tubular needle element 63 projecting in the direction of the outlet opening 36 of the attachment member 19 which may be produced from the same plastics material as the support member element 62 or else be formed by a metal element co-moulded in the support member element 62, or from the same material as the support member element, for example metal. This needle element 63 is provided with an oblique end surface at its end 64 facing towards the outlet opening 36. If the needle protection cap 25 is now separated by breaking the score line 23 and removed, the support member element 62 may be pushed forward in the direction of the diaphragm 38 by a combined longitudinal and rotary displacement indicated by arrows 65 and 66, so that the end 64 pierces the diaphragm 38. Depending on the nature of the diaphragm, the same may be separated or merely pierced. A direct communication is established in this manner between the syringe needle channel 39 of the syringe needle 30 and the outlet opening 36. If, furthermore, the needle element 63 or an appropriate attachment member is sealingly located in the needle carrier 61, the sterility is retained absolutely during the opening displacement and longitudinal displacement of the support member element 62 in the direction of the arrow 66.

Merely for the record, let it be pointed out that it is evidently also possible to perform the piercing of the diaphragm merely by a longitudinal displacement in the direction of the arrow 66 instead of the combined longitudinal and rotary displacement according to the arrows 65 and 66, or in the case of an appropriate configuration, for example by an arrangement of the diaphragm 38 made obliquely to the longitudinal direction of the outlet opening 36, to open this diaphragm 38 merely by a rotation of the support member element 62.

In modification of the embodiment illustrated in FIG. 5, it is also possible however to install a solid needle in the centre of the injection channel of the needle carrier 61, with which the diaphragm 38 is pierced, instead of the tubular needle element 63, so that the injection fluid may penetrate into the syringe needle channel 39 through the opening thus made.

The structure and arrangement of the closure device and of the opening member associated with the same are evidently wholly unaffected by the structure of the opening device of the needle protectin device, and vice versa. In a logical manner, additional advantages and actions result however from the combination of these two solutions, in which connection however, the incorporation of two opening devices formed by score lines for example, in the extension of a needle protection cap 25, may represent an independent invention.

I claim:

1. An injection syringe comprising
   (a) a syringe body adapted to receive an injectin fluid;
   (b) a frusto-conically tapered attachment member integral with the syringe body,
      (1) the syringe body and the attachment member defining an annular groove therebetween, and
      (2) the attachment member defining an outlet opening for the injection fluid in communication with the syringe body;
   (c) a membrane closing the outlet opening;
   (d) a syringe needle arranged coaxially with the outlet opening;
   (e) a tubular needle element arranged coaxially with the outlet opening and in communication with the syringe needle, the tubular needle element having an end facing the membrane and the membrane being interposed between the tubular needle element end and the outlet opening;
   (f) a two-part protective cap for the syringe needle,
      (1) one part of the cap constituting a securing device for the cap and including inwardly projecting claw means resiliently engaging the annular groove,
      (2) a second part of the cap constituting a needle protection cap, and
      (3) a weakened score line frangibly connecting the parts of the protective cap; and
   (g) a two-part device for breaking the membrane whereby the outlet opening communicates with the tubular needle element, the two-part membrane breaking device extending in the interior of the protective cap from the attachment member past the score line to the needle protection cap and essentially consisting of
      (1) a needle carrier part joined to the protective cap and defining an axial bore having an open end facing the membrane;
      (2) a support member part joined to the tubular needle element, the support member holding the syringe needle and the support member with the tubular needle element being displaceably guided in the needle carrier part relative to the membrane in a direction of the longitudinal extension of the syringe needle for piercing the membrane, and
      (3) the tubular needle element being sealingly and slidably guided in the needle carrier.

2. The injection syringe of claim 1, wherein the tubular needle element is integral with the syringe needle.

3. The injection syringe of claim 1, wherein the needle carrier is welded to the protective cap.

* * * * *